United States Patent [19]

Minami

[11] Patent Number: 4,960,914
[45] Date of Patent: Oct. 2, 1990

[54] METHOD FOR THE PREPARATION OF NAPHTHOQUINONE

[75] Inventor: Ryohei Minami, Ibaragi, Japan

[73] Assignee: Sumitomo Metal Industries, Ltd., Osaka, Japan

[21] Appl. No.: 300,695

[22] Filed: Jan. 19, 1989

Related U.S. Application Data

[63] Continuation of Ser. No. 751,979, Jun. 28, 1985, abandoned.

[30] Foreign Application Priority Data

Jun. 29, 1984 [JP] Japan ................. 59-135591

[51] Int. Cl.$^5$ ............... C07C 46/04; C07C 50/12
[52] U.S. Cl. ................... 552/296; 502/218
[58] Field of Search .......... 260/396 R; 502/218; 552/296

[56] References Cited

U.S. PATENT DOCUMENTS

| | | | |
|---|---|---|---|
| 2,765,323 | 10/1956 | Dixon et al. | 260/396 R |
| 3,095,430 | 6/1963 | Wettstein | 260/396 R |
| 4,032,548 | 6/1977 | Martin et al. | 260/396 R |
| 4,035,399 | 7/1977 | Yokoyama et al. | 260/396 R |
| 4,111,967 | 9/1978 | Martin et al. | 260/396 R |

*Primary Examiner*—Vivian Garner
*Attorney, Agent, or Firm*—Burns, Doane, Swecker & Mathis

[57] ABSTRACT

A catalyst for use in vapor phase oxidation of naphthalene into 1,4-naphthoquinone is dislosed. The catalyst which is supported on an inert carrier material is represented by the formula:

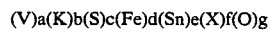

$$(V)_a(K)_b(S)_c(Fe)_d(Sn)_e(X)_f(O)_g$$

where V, K, S, Fe, Sn and O stand for vanadium, potassium, sulfur, iron, tin and oxygen, respectively; X stands for at least one element such as silicon, titanium or aluminum which serves as a carrier in the form of oxide; and a, b, c, d, e, f and g are the atomic fractions of the respective elements wherein the ratio of a:b:c:d:e:f = 10:10–100:5–100:0.1–10:0.05–10:10–300. Using the above catalyst the vapor phase oxidation can be effected at a relatively low temperature of not higher than 500° C., usually not higher than 420° C., resulting in the formation of 1,4-naphthoquinone in a high yield and with a high selectivity.

6 Claims, No Drawings

METHOD FOR THE PREPARATION OF NAPHTHOQUINONE

This application is a continuation, of application Ser. No. 751,979, filed June 28, 1985, now abandoned.

BACKGROUND OF THE INVENTION

The present invention relates to a method for preparing 1,4-naphthoquinone (hereinafter merely referred to as naphthoquinone) which is useful as a starting material for the synthesis of various dyes and organic compounds. More particularly it relates to a method for the preparation of naphthoquinone by catalytic vapor phase oxidation of naphthalene as well as a catalyst suitable for use in such a method and processes for the preparation of such a catalyst.

Naphthoquinone is generally prepared by vapor phase oxidation of naphthalene with a molecular oxygen-containing gas in the presence of a catalyst in a fixed bed-type reactor to form 1,4-naphthoquinone. A catalyst which has been proposed as effective for this purpose is prepared by mixing active ingredients comprising vanadium pentoxide, potassium sulfate and potassium pyrosulfate with a carrier material such as silicic acid or diatomaceous earth and then shaping and calcining the mixture.

For example, Japanese Patent Publication No. 5533/1976 discloses the use of a ternary system catalyst for the preparation of naphthoquinone comprising potassium sulfate, potassium pyrosulfate and vanadium pentoxide on a carrier wherein the pore size distribution of the carrier is controlled so as to improve the catalytic activity. Japanese Patent Publication No. 15063/1968 discloses the use of a similar catalyst on a carrier which has been calcined at a high temperature prior to supporting the active ingredients thereon. It also discloses that the catalyst may optionally contain tungsten to further improve the activity. Other catalysts of the above basic ternary system known in the art include one whose carrier has a specific pore volume and pore size distribution (Japanese Patent Laid-Open Application No. 34353/1972), one comprising a carrier in agglomerated form prepared by washing diatomaceous earth with an acid (Japanese Patent Publication No. 22559/1976), and one further containing iron as an essential element to improve the yield of the naphthoquinone product.

These prior art catalysts for the preparation of naphthoquinone have many problems. The conversion of a catalyst of this type is not compatible with the selectivity thereof toward the desired naphthoquinone; a catalyst capable of providing a higher conversion of naphthalene in order to produce naphthoquinone with a higher yield tends to have decreased selectivity, while a catalyst capable of producing naphthoquinone with a higher selectivity tends to have decreased conversion so that the amount of unreacted naphthalene is increased, which is accompanied by an increased load in a succeeding separation step for isolating the reaction product from the unreacted naphthalene. Moreover, with these catalysts, if one can obtain increased conversion of naphthalene to improve the yield of naphthoquinone, the reaction must be conducted at a relatively high temperature in the range of from 420° to 450° C., which inevitably makes the temperature control complicated.

As the reaction temperature increases, undesirable consecutive oxidative reactions of the naphthoquinone product may occur more readily, resulting in the formation of by-products such as phthalic anhydride, maleic anhydride, CO, and $CO_2$ in increased amounts, thereby decreasing the yield of naphthoquinone. It is said that the presence of sulfur in the catalyst in the form of $S_2O_7$ or similar solid sulfur oxide is essential for the formation of naphthoquinone from naphthalene. However, a loss of sulfur by escaping out of the system as gaseous $SO_x$ increases with increasing reaction temperature, thereby varying the composition of the catalyst and decreasing the selectivity toward naphthoquinone. Therefore, if a relatively high reaction temperature is employed, it may be necessary to carefully control the temperature such that the temperature does not rise significantly beyond the predetermined range, which involves rather complicated operation.

OBJECTS OF THE INVENTION:

An object of the invention is to provide a catalyst for use in vapor phase oxidation of naphthalene into naphthoquinone which is free from the above-mentioned problems encountered in prior art catalysts.

Another object of the invention is to provide a method for efficiently preparing naphthoquinone from naphthalene with a high yield at a relatively low temperature.

SUMMARY OF THE INVENTION:

In one aspect of the present invention, there is provided a catalyst for use in vapor phase oxidation of naphthalene into naphthoquinone comprising an inert carrier and active ingredients supported thereon, said catalyst being represented by the formula

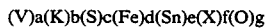

where
- V, K, S, Fe, Sn and O stand for vanadium, potassium, sulfur, iron, tin and oxygen, respectively;
- X stands for at least one element such as silicon, titanium or aluminum which serves as a carrier in the form of an oxide; and
- a, b, c, d, e, f, and g are the atomic fractions of the respective elements wherein the ratio of a:b:c:d:e:f = 10:10–100:5–100:0.1–10:0.05–10:10–300 and g is a value depending on the values of a–f and the form of each essential element present in the catalyst.

In another aspect, the present invention also provides a method for the preparation of naphthoquinone from naphthalene by vapor phase oxidation at a temperature of not higher than 500° C. in the presence of the above catalyst.

In a still further embodiment, the present invention provides processes for the preparation of the above catalyst. These processes include the steps of combining sources of the essential elements with a carrier material, and calcining the resulting mixture.

DETAILED DESCRIPTION OF THE PREFERRED EMBODIMENTS

We have studied from various viewpoints the activities of the vanadium pentoxide-potassium sulfate-potassium pyrosulfate ternary catalyst system to which one or more additional elements selected from titanium, zirconium, niobium, molybdenum, tungsten, thallium, tin, iron and the like are added. As a result of such catalyst screening test, we have found that a catalyst having a high activity at a relatively low temperature can be obtained by addition of iron and tin to the above basic ternary catalyst system.

In the above test, when iron was added to the basic vanadium pentoxide-potassium sulfate-potassium pyrosulfate ternary catalyst system, the selectivity toward naphthoquinone was improved while maintaining the conversion at the same level as that of the basic ternary system. When tin was added to the basic system, the conversion of naphthalene was improved decreasing the amount of unreacted naphthalene to advantage, but at the same time the selectivity toward naphthoquinone was decreased to a considerable extent. In contrast, when iron and tin were added together, both the conversion and the selectivity of the catalyst could be improved significantly.

On the basis of these findings, the catalyst employed in the present invention for the preparation of naphthoquinone is of a six-component system on a carrier in which iron and tin are added together as essential elements to the basic system consisting essentially of vanadium, potassium, sulfur and oxygen.

In accordance with the present invention, iron (Fe) is added so as to provide an atomic ratio of iron to vanadium in the range of from 0.1:10 to 10:10, preferably from 0.5:10 to 4:10, and most preferably from 1:10 to 3:10. Addition of too much iron, such as at an atomic ratio of iron to vanadium exceeding 10:10, tends to decrease the conversion, while an extremely low iron content such that the atomic ratio of iron to vanadium is less than 0.1:10, is not sufficient to exert its effect of improving the selectivity toward naphthoquinone.

Tin (Sn) when added in an amount sufficient to provide an atomic ratio of tin to vanadium in the range of from 0.05:10 to 10:10, preferably from 0.05:10 to 4:10, and most preferably from 0.1:10 to 2:10 is effective for improving the conversion of naphthalene. However, an extremely high tin content exceeding an atomic ratio of tin to vanadium of 10:10 may cause consecutive oxidation reactions of the resulting naphthoquinone to decrease the yield of naphthoquinone. Like iron, an excessively low tin content such that the atomic ratio of tin to vanadium is less than 0.05:10, is not effective for the purpose of the present invention.

Vanadium (V) is the most essential catalytic component in the oxidation catalyst system used herein. Therefore, the catalytic activity of the catalyst tends to increase with increasing vanadium content. However, addition of too much vanadium relative to the carrier such that the atomic ratio of vanadium to the carrier element (X in the foregoing formula) exceeds 10:10, does not provide a further increase in the catalytic activity due to agglomeration of vanadium. On the other hand, an extremely low vanadium content of less than 10:300 in the above atomic ratio is not sufficient to obtain the catalytic activity to a satisfactory extent due to a decrease of the active sites in the catalyst.

Potassium (K) serves to control the oxidative activity of vanadium and is added so as to provide an atomic ratio of potassium to vanadium in the range of from 10:10 to 100:10, preferably from 10:10 to 50:10. If the atomic fraction of potassium is less than that of vanadium, then a burning reaction may take place to decrease the yield of the naphthoquinone product. On the other hand, a high potassium content of more than ten times the atomic fraction of vanadium tends to decrease the oxidative activity of vanadium.

The sulfur (S) component is present in the catalyst as pyrosulfate ($S_2O_7$) and sulfate ($SO_4$) of one or more metallic elements of the catalyst. This component is essential for developing and controlling the oxidative activity of vanadium in the catalyst. In order to maximize the yield of naphthoquinone, it is advantageous to optimize the $S_2O_7/SO_4$ ratio in the catalyst. Preferably the $S_2O_7/SO_4$ ratio is at least 0.05, and more preferably within the range of from 0.1 to 0.7. The $S_2O_7SO_4$ ratio referred to herein is that of the mixture of the active ingredients before calcination from which the final catalyst is prepared by calcination. The total sulfur content of the catalyst is generally such that the atomic ratio of sulfur to vanadium is within the range of from 5:10 to 100:10, preferably from 5:10 to 50:10, and more preferably from 5:10 to 30:10. The total sulfur content and the $S_2O_7/SO_4$ ratio of the catalyst will vary depending on such parameters as the amounts of potassium sulfate, potassium pyrosulfate, and other sulfate or pyrosulfate compounds incorporated in the catalyst, calcination conditions (for the total sulfur content) and the like. Therefore, these parameters are selected so as to provide an optimum $S_2O_7/SO_4$ ratio and sulfur content.

The active ingredients of the catalyst of the present invention are supported on a carrier material such as silica, titania, alumina, diatomaceous earth or the like. Each of these carrier materials may be used alone. Alternatively, two or more of these materials may be combined to serve as a carrier. Of these materials, usually silica such as silica xerogel including silica gel, or white carbon is employed most widely as a carrier in a catalyst for the preparation of naphthoquinone.

Silica gel may be prepared from a commercially available silica sol by adding thereto dropwise a mineral acid such as sulfuric acid to deposit precipitates, which are then dried to give silica gel. In general, if the carrier after shaping and calcination of the catalyst possesses too many micropores having a radius of approximately 3000 Å or smaller, undesirable consecutive oxidation reactions and burning reactions of the naphthoquinone product are accelerated, resulting in a decreased yield of naphthoquinone. Therefore, the silica gel used as a carrier preferably possesses macropores having a radius of greater than approximately 3000 Å at as a high proportion as possible after the catalyst supported thereon is shaped and calcined. In order to improve the conversion of naphthalene, it is preferred that the carrier have a larger pore volume comprised predominantly of macropores as defined above. Preferably the carrier after calcination of the catalyst has a pore volume of at least about 0.1 ml/g as determined by the $N_2$ BET method. Also, it is preferred that at least 50%, and more preferably at least 80% of the pores be macropores as defined above.

The catalyst according to the invention may be prepared from a wide variety of materials which serve as sources of the essential elements. The particular materials employed in the preparation of the catalyst are not critical in the invention and any suitable sources of the essential elements may be employed.

A preferred vanadium source is ammonium metavanadate which is decomposed at the calcination temperature to give vanadium oxide and it may be employed as a solution in a suitable solvent such as water or aqueous monoethanolamine. Other vanadium sources which produce vanadium pentoxide at the calcination temperature of the catalyst such as ammonium orthovanadate and pyrovanadate may also be used.

Potassium may be incorporated in the catalyst in the form of potassium sulfate and potassium pyrosulfate. As mentioned previously, it is preferable to select the $S_2O_7/SO_4$ ratio (of the pre-calcination mixture of active ingredients) so as to maximize the yield of naphthoquinone. Therefore, the relative amounts of potassium sulfate and pyrosulfate should be selected to give the desired $S_2O_7/SO_4$ ratio, although it is necessary to consider the amounts of other sulfates and pyrosulfates present in the catalyst system. Thus, when one or more metallic elements are added as sulfates, potassium sulfate may be omitted or may be added in a lesser amount. Of course, other potassium sources may be employed.

It is to be noted that a part of potassium pyrosulfate decomposes at the calcination temperature of the catalyst to form potassium sulfate and $SO_3$ gas as is known in the art. The catalyst after calcination therefore may have an $S_2O_7/SO_4$ ratio outside the range defined above for the pre-calcination mixture.

Iron is preferably added as $FeSO_4$, $Fe_2(SO_4)_3$, $Fe(OH)_2$, $Fe(NO_3)_2$, $Fe(NO_3)_3$, $FeCl_3$ or the like, while tin is preferably added in the form of $SnCl_2$, $SnCl_4$, $SnSO_4$, $Sn(SO_4)_2$, $SnO$, $SnO_2$ or the like. However, the iron and tin sources are not limited to these compounds and other suitable iron or tin compounds may be used.

Sulfur should be present in the catalyst as a sulfate and pyrosulfate, and it may come from the sources of other essential elements such as potassium sulfate and pyrosulfate, ferrous or ferric sulfate, and stannous or stannic sulfate.

The catalyst according to the invention may be prepared, by admixing the sources of the essential elements, for example, ammonium metavanadate, potassium pyrosulfate, potassium sulfate, tin sulfate and ferrous sulfate in a suitable medium such as water or aqueous monoethanolamine solution, preferably in an amount sufficient to give a solution. Since the solubility of ammonium metavanadate in water is not so high, it is convenient to first dissolve ammonium metavanadate in the solvent used and then add and dissolve the other ingredients to give a solution. The use of aqueous monoethanolamine as a solvent is preferable since it facilitates dissolution of ammonium metavanadate. Thereafter, a finely divided silica gel having a size of −100 mesh is added to the solution and mixed. The resulting mixture is then evaporated to dryness, dried, pulverized, shaped, and finally calcined to give a catalyst having the composition defined above.

Usually the catalyst is shaped into pellets or granules, e.g., cylindrical granules, with an appropriate shaping machine such as a tableting press. The dimensions of the cylindrical granules are, for example, about 5 mm in diameter and about 5 mm in length. However, the shape of the catalyst is not critical and any shape may be employed as long as it is suitable for use in catalyzing vapor phase reactions. The pellets (e.g., cylindrical granules) of the catalyst may have one or more holes in each pellet to reduce the pressure drop which may be encountered during a vapor phase catalytic reaction in a fixed bed reactor.

The final calcination step is commonly conducted at a temperature of from 300° to 600° C., and preferably from 400° to 500° C. for a period of from 3 to 48 hours, and preferably from 3 to 24 hours. During the calcination, some ingredients present in the catalyst such as potassium pyrosulfate and ammonium metavanadate will partly decompose to form potassium sulfate and vanadium pentoxide, respectively.

Alternatively, after the sources of the essential elements such as a solution of ammonium metavanadate in aqueous monoethanolamine, potassium pyrosulfate, potassium sulfate, tin sulfate and ferrous sulfate are admixed to give a solution and a finely divided silica gel is added to the solution and mixed, the mixture may be evaporated to dryness and subjected to a preliminary calcination at a relatively low temperature on the order of 300° C. To the resulting powdery mixture a sufficient amount of water is added to form a slurry. The slurry is then sprayed onto the surface of silicon carbide balls and the balls thus coated with the catalyst are calcined under the conditions mentioned above regarding the final calcination step.

According to the method for the preparation of naphthoquinone of the invention, naphthalene is subjected to vapor phase oxidation in a molecular oxygen-containing atmosphere in the presence of a catalyst prepared in the above manner to form 1,4-naphthoquinone. Due to the high activity of the catalyst, the vapor phase oxidation may be effected at a relatively low temperature of not higher than 500° C., usually in the range of 250°–500° C., preferably in the range of 300°–450° C. and more preferably in the range of 380°–440° C., whereby consecutive oxidation of the naphthoquinone product can be minimized resulting in the formation of the desired product in a high yield.

The catalytic vapor phase oxidation may be effected either in a fixed bed or fluidized bed reactor. For example, a tube reactor may be packed with the catalyst prepared so as to have a particle diameter of about 5 mm and a composition as defined herein, and a gas containing molecular oxygen and naphthalene may be passed through the tube reactor at a temperature of 250° to 500° C. and at a space velocity of from 1000 to 6000 $hr^{-1}$, preferably from 1000 to 3000 $hr^{-1}$ to oxidize naphthalene into naphthoquinone. The gas to be passed through the packed reactor preferably contains from 0.5% to 1.5% by volume of naphthalene in addition to molecular oxygen, and such a gas may be prepared by adding naphthalene vapor to air. For example, air may be passed through a vessel containing solid naphthalene granules to obtain a naphthalene containing air.

Alternatively, in place of the above fixed bed reactor, a conventional fluidized bed reactor may be used in the catalytic vapor phase oxidation of naphthalene.

During the catalytic oxidation reaction, a small amount of steam may be added to the gas in order to control the reaction temperature more effectively.

The following examples are given as specific illustrations of the invention. It should be understood, however, that the invention is not limited to the specific details set forth therein.

EXAMPLE 1

To a silica sol heated at 40° C., a 3% sulfuric acid solution was added dropwise in an amount sufficient to give a pH of 8, and the deposited precipitates were collected and calcined at 95° C. The resulting silica gel was dried for 2 days at 105° C. and pulverized to −100 mesh. The thus obtained silica gel (92 g) was added to a solution consisting of 101.5 g of potassium pyrosulfate, 5.56 g of ferrous sulfate heptahydrate, 4.30 g of stannous sulfate, and 186 ml of a solution of ammonium metavanadate (prepared by dissolving 44 g of ammonium metavanadate in 700 ml of an aqueous monoethanolamine solution) which had been prepared by mixing all the ingredients at 80° C. The silica gel-containing mixture was stirred and then dried for 18 hours at 105° C. to leave a cake. After the entire cake was pulverized to —100 mesh, the resulting powder was lubricated with 1.5% by weight of powdery graphite based on the catalyst powder and tabletted into cylindrical granules 5 mm in diameter and 5 mm in length. The granules were then calcined for 5 hours at 450° C. to give a catalyst (hereinafter referred to as Catalyst A). The composition of Catalyst A was as follows:

$$V_{10}K_{80}S_{24}Fe_2Sn_2Si_{170}$$

A tube reactor having an inner diameter of 20 mm was packed with 16 cc of Catalyst A and air containing 0.7 vol.% of naphthalene was passed through the reactor at various temperatures and at a flow rate of 440 Ncc/min (equivalent to a space velocity of 1650 hr$^{-1}$). The effluent gas from the reactor was passed through acetone to recover the products and unreacted naphthalene. The acetone solution thus obtained was analyzed by gas chromatography to determine the yield of each product. The results are summarized in Table 1 below.

As is apparent from the results shown in Table 1, the maximum yield of naphthoquinone (33 mol% or 40 wt.%) could be obtained at a relatively low reaction temperature of 380° C.

TABLE 1

| | (Catalyst A) | | |
| --- | --- | --- | --- |
| | Yield (mol %) | | |
| Reaction Temperature | Naphtho-quinone | Phthalic Anhydride | Unreacted Naphthalene |
| 380° C. | 33 | 40 | 23 |

EXAMPLE 2

The procedure of Example 1 employed in the preparation of the catalyst was repeated except that the amounts of tin and iron were varied and the resulting catalysts were used to oxidize naphthalene in the same manner as described in Example 1. The oxidation reaction in this example was effected at a temperature of 380° C. and a space velocity of 1650 hr$^{-1}$. The results are shown in Table 2 in terms of the yield of each product.

As can be seen from Table 2, the catalyst which contained iron but which was free from tin (Catalyst No. 1) could not provide a high conversion of naphthalene; 60% of the naphthalene introduced into the reactor remained unreacted. On the other hand, the catalyst which contained tin but which was free from iron (Catalyst No. 3) produced phthalic anhydride as a by-product at a high proportion and the desired naphthoquinone with a low yield, although it could provide a high conversion of naphthalene. In contrast, the presence of both iron and tin in the catalyst system was effective for increasing the yield of naphthoquinone and the catalyst which contained iron and tin (Catalyst No. 2) could produce the desired naphthoquinone with the highest yield.

TABLE 2

| | | Yield (mol %) | | |
| --- | --- | --- | --- | --- |
| Catalyst No. | Composition | Naphtho-quinon | Phthalic Anhy-dride | Unreacted Naphtha-lene |
| 1 | $V_{10}K_{80}S_{22}Fe_2Si_{170}$ | 20 | 18 | 60 |
| 2 | $V_{10}K_{80}S_{25}Fe_2Sn_4Si_{170}$ | 32 | 50 | 13 |
| 3 | $V_{10}K_{80}S_{28}Sn_2Si_{170}$ | 18 | 60 | 16 |

EXAMPLE 3

A solution obtained by admixing 203 g of potassium pyrosulfate, 11.1 g of ferrous sulfate heptahydrate, 8.6 g of stannous sulfate and 744 ml of a solution of ammonium metavanadate in aqueous monoethanolamine (prepared by dissolving 44 g of ammonium metavanadate in 700 ml of an aqueous monoethanolamine solution) at 80° C. was combined with 184 g of silica gel prepared in the same manner as described in Example 1 and the resulting mixture was stirred and then dried at 105° C. to leave a cake. After the cake was preliminarily calcined for 1 hour at 300° C., 1 liter of water was added to the resulting powder to make a slurry. Onto the surface of heated silicon carbide balls having a diameter of 5 mm and a pore volume of 0.1 ml/g as measured by a mercury porosimeter, the slurry was sprayed to coat the balls. The coated silicon carbide balls were then subjected to final calcination to give a finished catalyst (hereinafter referred to as Catalyst B) having the following composition:

$$V_{10}K_{40}S_{13}Fe_1Sn_1Si_{170}$$

In the presence of Catalyst B, catalytic vapor phase oxidation of naphthalene was conducted at a space velocity of 650 hr$^{-1}$ following the procedure employed in Example 1. The yields of the products are summarized in Table 3 below.

It can been seen from the results shown in Table 3 that the use of a catalyst coated on the surface of silicon carbide serves to suppress a consecutive oxidation reaction of naphthoquinone into phthalic anhydride, thereby providing a higher catalytic activity and an improved yield of naphthoquinone.

TABLE 3

| | (Catalyst B) | | |
| --- | --- | --- | --- |
| | Yield (mol %) | | |
| Reaction Temperature | Naphtho-quinone | Phthalic Anhydride | Unreacted Naphthalene |
| 400° C. | 41 | 42 | 10 |

EXAMPLE 4

Ammonium metavanadate (42.2 g) was dissolved in water and the pH of the solution was adjusted to 8 with sulfuric acid. To the solution, 55.0 g of potassium sulfate, 50.0 g of potassium pyrosulfate, 9.30 g of ferrous sulfate heptahydrate and 3.6 g of stannous sulfate were added and heated to 80° C. so as to completely dissolve the added salts therein. To the resulting solution, 56.0 g of silica gel powder having a true specific gravity of 2.2 and a pore volume of 0.54 cc/g as measured by the $N_2$ BET method was then added and the mixture was evaporated to dryness to leave a cake. The whole cake was pulverized to −100 mesh and the pulverized powder was lubricated by adding 1.5% by weight of graphite based on the weight of the powder. The lubricated powder was then shaped into cylindrical granules 5 mm in diameter and 5 mm in length and calcined for 15 hours at 450° C. to give a catalyst (hereinafter referred to as Catalyst C). The strength of Catalyst C was 5 Kg (measured by Kiya Hardness Tester) which was on the order acceptable for a catalyst for commercial use. The composition of Catalyst C was:

$$V_{10}K_{29}S_{18}Fe_2Sn_{0.4}Si_{26}.$$

Additional catalysts having a similar composition except for the tin content were also prepared in the same manner as above.

In the presence of Catalyst C or a similar catalyst prepared above, catalytic vapor phase oxidation of naphthalene was conducted at 400° C. and at a space velocity of 1650 hr$^{-1}$ following the procedure employed in Example 1. The yields of the products are summarized in Table 4 below.

As can be seen from Table 4, all the catalysts prepared in this example could produce naphthoquinone in a high yield at a relatively low temperature at 400° C.

TABLE 4

| | (Reaction Temperature: 400° C.) | | | |
|---|---|---|---|---|
| | | Yield (mol %) | | |
| Catalyst No. | Composition $V_{10}K_{29}S_{18}Fe_2Sn_xSi_{26}$ | Naphthoquinone | Phthalic Anhydride | Unreacted Naphthalene |
| 1 | $Sn_{0.4}$ (Catalyst C) | 42 | 44 | 8 |
| 2 | $Sn_2$ | 41 | 48 | 5 |
| 3 | $Sn_7$ | 40 | 52 | 3 |

COMPARATIVE EXAMPLE 1

The procedure of Example 4 was repeated except that neither ferrous sulfate nor stannous sulfate was added in the preparation of the catalyst. The catalyst prepared in this example (referred to as Catalyst D) had the following composition:

$V_{10}K_{29}S_{17}Si_{26}$.

The yields of the products of catalytic vapor phase oxidation of naphthalene in the presence of Catalyst D are shown in Table 5 below. As is apparent from Table 5, this comparative catalyst had a decreased yield of the desired naphthoquinone with an increased amount of unreacted naphthalene as compared with Catalyst C and similar catalysts prepared in Example 4 which contained both iron and tin.

TABLE 5

| | (Catalyst D) | | |
|---|---|---|---|
| | Yield (mol %) | | |
| Reaction Temperature | Naphthoquinone | Phthalic Anhydride | Unreacted Naphthalene |
| 400° C. | 30 | 30 | 36 |

COMPARATIVE EXAMPLE 2

The procedure of Example 4 was repeated except that only stannous sulfate was omitted in the preparation of the catalyst. The catalyst prepared in this example (referred to as Catalyst E) had the following composition:

$V_{10}K_{29}S_{18}Fe_2Si_{26}$.

The yields of the products of catalytic vapor phase oxidation of naphthalene in the presence of Catalyst E are shown in Table 6 below. As is apparent from Table 6, this catalyst which contained iron but which was free from tin had a decreased yield of the desired naphthoquinone with an increased amount of unreacted naphthalene as compared with Catalyst C prepared in Example 4 which contained both iron and tin, although it produced a slightly higher yield of naphthoquinone than Catalyst D which were free from both iron and tin.

TABLE 6

| | (Catalyst E) | | |
|---|---|---|---|
| | Yield (mol %) | | |
| Reaction Temperature | Naphthoquinone | Phthalic Anhydride | Unreacted Naphthalene |
| 400° C. | 32 | 33 | 30 |

As is apparent from the foregoing Examples, according to the method of the present invention, it is possible to prepare naphthoquinone by catalytic vapor phase oxidation of naphthalene at a relatively low temperature in a sufficiently high yield so that the unreacted naphthalene can be separated from the reaction mixture with a reduced load on the separation equipment. Also, due to the relatively low reaction temperature, the oxidation reaction can be effected without complicated temperature control to minimize side reactions. A sufficiently high selectivity toward the desired naphthoquinone was also attained according to the method of the invention. Thus, the catalyst and the method for the preparation of naphthoquinone according to the present invention have beneficial effects on the commercial production of naphthoquinone which is useful as a starting material for the preparation of various dyes and organic compounds.

Although the invention has been described with respect to preferred embodiments, it is to be understood that variations and modifications may be employed as will be apparent to those skilled in the art. Such variations and modifications are to be considered within the scope of the claims appended hereto.

What is claimed is:

1. A method for the preparation of 1,4-naphthoquinone from naphthalene which comprises subjecting naphthalene to vapor phase oxidation at a temperature of not higher than 500° C. in a molecular oxygen-containing atmosphere in the presence of a catalyst comprising an inert carrier and active ingredients supported thereon said catalyst being represented by the formula:

(V)a(K)b(S)c(Fe)d(Sn)e(X)f(O)g where
V, K, S, Fe, Sn and O stand for vanadium, potassium, sulfur, iron, tin and oxygen, respectively;
X stands for at least one element selected from the group of silicon, titanium and aluminum which serves as a carrier in the form of an oxide; and
a, b, c, d, e, f, and g are the atomic fractions of the respective elements wherein the ratio of a:b:c:d:e:f + 10:10–100:5–30:1–3:0.1–2:10–300 and g is a value depending on the values of a–f and the form of each essential element present in the catalyst.

2. The method as defined in claim 1 wherein the reaction temperature is in the range of 250°–500° C.

3. The method as defined in claim 2 wherein the reaction temperature is in the range of 300°–450° C.

4. The method as defined in claim 1 wherein the vapor phase oxidation is carried out by passing a gas which contains oxygen and naphthalene through a fixed bed of the catalyst at a temperature of not higher than 500° and at a space velocity in the range of 1000–6000 hr$^{-1}$.

5. The method as defined in claim 4 wherein the space velocity of the gas is in the range of 1000–3000 hr$^{-1}$.

6. The method as defined in claim 1 wherein a small amount of steam is present in the molecular oxygen-containing atmosphere.

* * * * *